(12) United States Patent
Joyce et al.

(10) Patent No.: US 7,157,443 B2
(45) Date of Patent: Jan. 2, 2007

(54) STAPHYLOCOCCUS AUREUS EXOPOLYSACCHARIDE AND PROCESS

(75) Inventors: Joseph G. Joyce, Lansdale, PA (US); James C. Cook, III, Lansdale, PA (US); Chitrananda Abeygunawardana, Ambler, PA (US); Karen M. Grimm, Duryea, PA (US); Craig T. Przysiecki, Lansdale, PA (US); Robert W. Hepler, Harleysville, PA (US); Charlotte C. Ip, Blue Bell, PA (US); Keith Roper, Salt Lake City, UT (US); Qiuwei Xu, West Chester, PA (US); Kathrin U. Jansen, Doylestown, PA (US); Paul M. Keller, Lansdale, PA (US); Leslie D. Cope, Hatfield, PA (US)

(73) Assignee: Merck & Co., Inc., Rahway, NJ (US)

( * ) Notice: Subject to any disclaimer, the term of this patent is extended or adjusted under 35 U.S.C. 154(b) by 100 days.

(21) Appl. No.: 10/498,070

(22) PCT Filed: Dec. 6, 2002

(86) PCT No.: PCT/US02/39079

§ 371 (c)(1),
(2), (4) Date: Jun. 9, 2004

(87) PCT Pub. No.: WO03/053462

PCT Pub. Date: Jul. 3, 2003

(65) Prior Publication Data

US 2004/0259838 A1 Dec. 23, 2004

Related U.S. Application Data

(60) Provisional application No. 60/346,755, filed on Dec. 11, 2001, provisional application No. 60/355,941, filed on Feb. 11, 2001.

(51) Int. Cl.
*A61K 31/715* (2006.01)
*A61K 39/02* (2006.01)
*C07H 1/00* (2006.01)

(52) U.S. Cl. .................. 514/54; 536/53; 536/55.3; 536/123.1; 536/124; 424/234.1

(58) Field of Classification Search .................. 514/54; 536/53, 55.3, 123.1, 124; 424/234.1
See application file for complete search history.

(56) References Cited

U.S. PATENT DOCUMENTS

| 4,695,624 A * | 9/1987 | Marburg et al. ........ 424/197.11 |
| 5,770,208 A | 6/1998 | Fattom et al. |
| 2002/0119166 A1 | 8/2002 | Pier et al. |

FOREIGN PATENT DOCUMENTS

| WO | WO 93/14784 | 8/1993 |
| WO | WO 00/03745 | 1/2000 |

OTHER PUBLICATIONS

McKenney, David et al., "Broadly Protective Vaccine for *Staphylococcus aureus* Based on an in Vivo-Expressed Antigen", Science, vol. 284, pp. 1523-1527 (1999).
McKenney, David et al., "The *ica* Locus of *Staphylococcus epidermidis* Encodes Production of the Capsular Polysaccharide/Adhesin", Infection and Immunity, vol. 66, No. 10, pp. 4711-4720 (1998).
Mack, Dietrich et al., "The Intercellular Adhesin Involved in Biofilm Accumulation of *Staphylococcus epidermidis* Is a Linear Beta-1,6-Linked Glucosaminoglycan: Purification and Structural Analysis", Journal of Bacteriology, vol. 178, No. 1, pp. 175-183 (1996).
Abeygunawardana et al., "Determination of the Chemical Structure of Complex Polysaccharides by Heteronuclear NMR Spectroscopy", Advances in Biophysical Chemistry, vol. 3, pp. 199-249 (1993).

* cited by examiner

*Primary Examiner*—Shaojia Anna Jiang
*Assistant Examiner*—Michael C. Henry
(74) *Attorney, Agent, or Firm*—Joan E. Switzer; Joanne M. Giesser (57) ABSTRACT

A high molecular weight polysaccharide intracellular adhesin (SAE) antigen having the general structure of poly-1,6,β-2-amidoglucopyranoside, which is variable substituted with N-acetyl and O-succinyl substituents is described. Also, a method is given for isolating this antigen from *Staphylococcus aureus*. The SAE can be used in a vaccine, either alone, conjugated to an immunogenic protein, and/or with an immunogenic adjuvant.

13 Claims, 7 Drawing Sheets

FIGURE 1.

Compositional analysis of purified PIA preparations

| Property | Component Percent by Mass | | |
|---|---|---|---|
| | native PIA | HF-PIA | AEC-PIA |
| GlcNH$_2$ [a] | | | |
|     N-acetyl | 57 | 53 | 55 |
|     Free amino | 43 | 47 | 47 |
| O-linked succinate | | | |
|     HPAEC-PAD | 9 | 1.2 | 8 |
|     NMR | 8 | 0.2 | 17 |
| N-linked succinate [a] | ND[d] | ND | ND |
| Glycerol phosphate[b] | 2 | ND | ND |
| Polyphosphoglycerol [a] | 5 | ND | ND |
| DNA [c] | 4 | Na[e] | ND |

FIGURE 2.
HPSEC analysis of purified PIA preparations.

| Quantitative Method | Molecular Mass (Da) | | | |
|---|---|---|---|---|
| | native-PIA | HF-PIA | AEC-PIA (intact) | AEC-PIA (sized) |
| Pollulan Standard Calibration[a] | 345,615 | 67,994 | 258,934 | (2,500,667)[c] 73,108 |
| MALLS/RI[b] | 640,000 | 135,000 | 445,000 | (19,000,000) 167,000 |

FIGURE 3

Hemagglutination by PIA polysaccharide forms.

| PIA preparation | $M_r$ (Da) [a] | HA (μg/ml) [b] |
|---|---|---|
| Native PI | 345,615 | 0.625 |
| HF-PIA | 67,994 | 2.500 |
| AEC-PIA (intact) | 258,934 | 0.312 |
| AEC-PIA (sized) | 73,108 | 0.625 |

FIGURE 4

Characterization of activated OMPC and PIA preparations

| Property | activated OMPC | AEC-PIA (intact) | AEC-PIA (sized) |
|---|---|---|---|
| thiol:lysine (mol:mol)[a] | 0.44 | NA[e] | NA |
| maleimide: GlcNH$_2$ (mol:mol)[b] | NA | 0.151 | 0.161 |
| side chain loading (% w/w)[c] | NA | 4.8 | 9.9 |
| GlcNH$_2$:protein (% w/w)[d] | 1 | 11 | 13 |
| N-acetyl glucosamine | NA | 50.5 | 50.0 |
| free glucosamine | NA | 49.5 | 50.0 |
| O-succinate | NA | 1.1 | 1.0 |

| Immunogen | ELISA titers with Native PIA | | |
|---|---|---|---|
| | Day -2 GMT | Day 21 GMT | Day 28 GMT |
| 8 ug Native PIA-OMPC | 229 | 102479 | 204800 |
| 0.8 ug Native PIA-OMPC | 114 | 117626 | 135117 |
| 0.08 ug Native PIA-OMPC | 131 | 22286 | 58813 |
| 0.008 ug Native PIA-OMPC | 174 | 2111 | 9700 |
| 8 ug Sized PIA-OMPC | 174 | 204800 | 270235 |
| 0.8 ug Sized PIA-OMPC | 151 | 67558 | 155209 |
| 0.08 ug Sized PIA-OMPC | 174 | 16889 | 77604 |
| 0.008 ug Sized PIA-OMPC | 263 | 2785 | 8444 |
| 1X Merck Aluminum Adjuvant | 151 | 303 | 263 |

STAPHYLOCOCCUS AUREUS EXOPOLYSACCHARIDE AND PROCESS

CROSS-REFERENCE TO RELATED APPLICATIONS

This application claims the benefit of U.S. Provisional Application No. 60/346,755, filed Dec. 11, 2001, and U.S. Provisional Application No. 60/355,941, filed Feb. 11, 2001, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

This invention relates to a new high molecular weight *Staphylococcus aureus* exopolysaccharide antigen (SAE), having the general structure of poly 1,6β-2 amidoglucopyranoside variably substituted with N-acetyl and O-succinyl substituents, and to processes for producing it. It also pertains to vaccines made using this SAE antigen.

BACKGROUND OF THE INVENTION

*Staphylococcus aureus* and *S. epidermidis* are important human pathogens, accounting for the majority of nosocomial sepsis cases reported each year. Both are associated with colonization of implanted medical devices, leading to systemic bacteremia and potentially fatal conditions such as endocarditis and ventilator-associated pneumonia. Due to the increase in the number of organisms exhibiting antibiotic resistance, particularly methicillin and vancomycin resistant *S. aureus* strains, new avenues of protection are sought. Of particular appeal are bacterial vaccines that target surface molecules known to be important in mediating initial steps of adherence and accumulation.

The primary stages of attachment and accumulation have mostly been studied in the coagulase negative staphylococci (CoNS) such as *S. epidermidis*. While initial attachment occurs mainly through non-specific interaction with bacterial surface proteins, accumulation is predominantly mediated by bacterial exo-polysaccharides. These surface-expressed carbohydrates may be attractive targets for vaccine-based strategies.

One staphylococcal carbohydrate of interest is the polysaccharide intercellular adhesin (PIA). PIA has been shown to be a major constituent of biofilm, an amorphous exopolysaccharide produced during the accumulation phase of growth. It is responsible for mediating cell-cell adhesion and may function to shield the growing colony from host immune defenses.

PIA isolated from *S. epidermidis* has been characterized by Mack et al, 1996 J. Bact. 178(1): 175–183. It is a polymer of molecular mass less than 30,000 Da, composed of β-1,6-linked glucosamine. Approximately 85% of the amino groups are substituted with N-acetate, and a minor proportion of the sugar hydroxyl groups are esterified with phosphate and succinate.

PIA production is associated with the ica gene locus and has been demonstrated in vitro under certain defined growth conditions for several CoNS strains. Recent reports have shown that other *staphylococcus* species, including *S. aureus*, contain the ica locus. Some of these were able to elicit biofilms in culture while others did not. All of the environmental factors affecting regulation of ica are not known, and a major impediment to the development of polysaccharide-based vaccines has been the sensitivity of their expression to growth conditions. Hence, it has been difficult to show with certainty that organisms grown in vitro produce the same surface polysaccharides as those present in an in vivo infection. Finally, accurate structural characterization of polysaccharide preparations has often been hampered by residual media contaminants, and this has occasionally led to identification of what were believed to be novel antigens.

It would therefore be desirable to have a simplified, robust process for the production of SAE in high amounts to facilitate vaccine production. Furthermore, it would be desirable to have chemical characterization of isolated SAE from sources other than *S. epidermidis*, namely, from *S. aureus*.

SUMMARY OF THE INVENTION

This invention provides an isolated *Staphylococcus aureus* high weight exopolysaccharide antigen (SAE) having the formula wherein 40–60% of $R_1$ is H and the remainder of $R_1$ if $COCH_3$ and 75–95% of $R_2$ is H and the remainder of $R_2$ if $C_4H_6O_4$, and n is such that the molecular weight is at least about 100,000 Da, preferably at least about 200,000 Da, and most preferably at least about 300,000 Da.

In a preferred embodiment, approximately 45–55% of $R_1$ is H, and approximately 85–95% of $R_2$ is H. In a particularly preferred embodiment of this invention, approximately 50% of $R_1$ is H, and approximately 85–95% of $R_2$ is H.

Another aspect of this invention is a purified *Staphylococcus aureus* high weight exopolysaccharide (SAE) having the formula wherein 40–60% of $R_1$ is H and the remainder of $R_1$ is $COCH_3$; and 75–95% of $R_2$ is H and the remainder of $R_2$ is $C_4H_6O_4$, and n is such that the molecular weight is at least about 100,000 Da, preferably at least about 200,000 Da, and most preferably at least about 300,000 Da. Preferably the SAE is in a preparation which is at least about 75% pure, preferably at least about 80% pure, and more preferably more than about 80% pure.

In a preferred embodiment, in the purified SAE, approximately 45–55% of $R_1$ is H, and approximately 85–95% of $R_2$ is H. In a particularly preferred embodiment of this invention, approximately 50% of $R_1$ is H, and approximately 85–95% of $R_2$ is H.

The isolated or purified SAEs of this invention may be used to make an immunogenic composition, i.e. a vaccine. The vaccine may used in any animal capable of producing an immunogenic response; and this invention specifically includes human vaccines as well as those suitable for veterinary purposes.

The immunogenic composition may contain the isolated and/or purified SAE in a physiologically acceptable salt solution. Additionally, in another embodiment, the SAE may be covalently coupled to an immunogenic protein carrier. Optionally, the SAE immunogenic composition may further comprise an immunostimulatory adjuvant.

A further aspect of this invention is a method of inducing an immune response in an animal comprising administering one of the SAE immunogenic compositions (SAE alone, SAE conjugated to an immunogenic protein carrier, and/or in the presence of an adjuvant).

Also provided for in this invention is a method of making a SAE compound having the formula wherein 40–60% of $R_1$ is H and the remainder of $R_1$ is $COCH_3$; and 75–95% of $R_2$ is H and the remainder of $R_2$ is $C_4H_6O_4$, and n is such that the molecular weight is at least about 100,000 Da, preferably at least about 200,000 Da, and most preferably at least about 300,000 Da comprising the steps of:

a) concentrating medium obtained from a *S. aureus* culture to obtain a concentrated medium;

b) filtering the concentrated medium to obtain a retentate; and c) digesting the retentate with a protease to obtain the SAE compound.

In another method according to this invention further comprises the steps of:

d) concentrating the SAE using diafiltration.

Optionally, the SAE compound can be subjected to a sizing chromatography step to produce a more uniformed-sized product.

In preferred embodiments, step a) comprises concentrating medium obtained from a *S. aureus* culture using tangential flow filtration. In another preferred embodiment, step b) comprises a diafiltration step.

Yet another aspect of this invention relates to a high molecular weight SAE antigen produced by the process of a) concentrating medium obtained from a *S. aureus* culture to obtain a concentrated medium;

b) filtering the concentrated medium to obtain a retentate; and c) digesting the retentate with a protease to obtain the SAE compound. Optionally, the SAE compound can be subjected to a sizing chromatography step to produce a more uniformed-sized product.

Further, this invention also related to immunogenic compositions comprising SAEs produced by this process. The SAEs produced by this process may be used in a suitable vaccine formulation; alternatively they may be covalently coupled to an immunogenic protein carrier.

BRIEF DESCRIPTION OF THE DRAWINGS

FIG. 1 shows the compositional analysis of the purified SAE preparation according to this invention. In the figure, [a]Measured by 1D 1H NMR. [b]Measured by HPAEC-PAD followed by conductivity detection on an IonPac AS11 column. Samples were hydrolyzed in 6N HCl at 95° C. for 72 hr. Quantification of the acid liberated glycerophosphate and succinate was achieved by comparing area of the glycerophosphate peak to area of a 4 nmol of hydrolyzed glycerophosphate and 0.5 nmol of hydrolyzed succinate standard. The linear detection range was 0.016 to 16 nmol for glycerophosphate and 0.016 to 1 nmol for succinate per injection. [c]Measured by absorbance at 260 nm. [d]Not detected. [e]Not assayed.

FIG. 2 shows the HPSEC analysis of purified SAE preparations. [a]Chromatography was performed as described in the Examples. For column calibration, a 50 µl injection of pollulan standards (4–7 mg/ml) covering the $M_r$ range 47,300 to 788,000 was made and the average retention time (RT) was calculated. A linear plot of $\log_{10} M_r$ vs $\log_{10}$ RT was constructed and the best fit line calculated by least squares regression. For SAE samples, a 75 µl injection of sample (1–3 mg/ml) was made and the estimated $M_r$ was determined by inputting the $\log_{10}$ RT into the standard curve equation. [b]Standard and sample injections were done as for [a]. Estimated $M_r$ was determined by selecting a narrow data set from the center of the refractive index peak and assuming a dn/dc value of 0.133. [c]Values in parentheses represent a minor component peak.

FIG. 3 shows results of hemagglutination by SAE polysaccharide forms. [a]Molecular mass determined relative to pollulan standards; refer to FIG. 2. [b]Hemagglutination defined as the minimal dilution of polysaccharide required to agglutinate a 1% suspension of sheep red blood cells after 2 hr at ambient temperature.

FIG. 4 shows characterizations of activated OMPC and SAE preparations. [a]Thiol content determined by reaction with 5,5'dithionitrobenzoic acid; protein concentration determined by modified Lowry assay. Lysine content was 0.4 μmol lys/mg protein. [b]Maleimide content determined by equivalency assay as described in Examples; glucosamine determined by HPAEC-PAD. [c]Determined by 1D $^1$H NMR using pulsed field gradient diffusion filtration as described. [d]Glucosamine determined by HPAEC-PAD. Values for conjugates were corrected for residual free polysaccharide as determined by physical mixing controls using activated SAE and non-activated OMPC (data not shown). [e]Not assayed.

FIGS. 6A and 6B show percent survival of mice who, after vaccination, were challenged with infection. FIG. 6A is Native SAE-OMPC, and FIG. 6B is Sized SAE-OMPC.

As used throughout the specification and claims, the following definitions will apply:

"High molecular weight" refers to a polymeric molecule having a molecular weight of at least about 100,000 Da, preferably at least about 200,000 Da, and more preferably at least about 300,000 Da.

"Isolated" means that the SAE has been separated from its native organism.

"Purified" or "Substantially pure" means that the SAE preparation which is assayed is at least about 75% pure, preferably at least about 80% pure, and more preferably more than about 80% pure.

"Native SAE" means SAE according to this invention, but which has not undergone a sizing step; its molecular weight is much larger than "Sized" SAE; Native SAE has a molecular weight ranging from approximately 300,000 to 700,000.

"Sized SAE" means SAE according to this invention which has undergone a sizing process, reducing its molecular weight to between 50,000 and 100,000.

DETAILED DESCRIPTION OF THE INVENTION

A recent report (McKeeney, et al 1999 Science 284: 1523–1527, which is hereby incorporated by reference) has described the identification of an antigen similar to SAE produced by both S. epidermidis and S. aureus. This antigen, termed poly-N-succinyl β-1,6 glucosamine (PNSG) or capsular polysaccharide adhesin (PS/A), allegedly has the same chemical backbone as SAE but contains primarily N-linked succinate instead of acetate, and has a high molecular mass (i.e. greater than 250,000 Da). The identification of a constitutively over-producing S. aureus mutant (strain MN8m, obtained from Brigham and Womens' Hospital) allowed purification of the antigen in sufficient quantities for physiochemical characterization and subsequent immunogenicity studies in mice. The McKeeney et al studies suggested that immune prophylaxis directed toward PNSG was broadly protective against both homologous and heterologous S. aureus challenge strains and that this protection was dependent on the presence of N-succinylation. Based on these studies, we sought to scale-up the production of PNSG for evaluation of its immunoprophylactic value in additional animal models. However, no antigen with the reported structure of PNSG was found.

In accordance with this invention, it was observed that strain MN8m produced a high molecular mass polymer which by chemical monosaccharide analysis and NMR was shown to be made of β-1,6 glucosamine substituted with approximately 50% N-linked acetate and 10% O-linked succinate. Further, we were able to show that the previous identification of the N-linked succinate component of the glycan was an artifact of the conditions used to hydrolyze the polymer prior to its NMR characterization. Chemical and physical size reduction of the polymer could produce a molecule of molecular mass approximately 50,000 Da or less. We conclude therefore that the product of the ica locus in the S. aureus strain MN8m is SAE.

Purification and Characterization of S. aureus SAE.

One aspect of this invention is a method of producing a large quantity of SAE polysaccharide from S. aureus and related species, including S. epidermidis, S. carnosus and other polysaccharide-producing members of the genus. In choosing the strain of S. aureus, it is desirable to use an overproducing strain, such as MN8, but other strains may be used. Fermentation conditions are often more important for achieving high productivity, and may be even more important than is choice of strain. For example, when MN8m was grown using chemically defined medium and conditions described by McKenney et al 1998 Infection and Immunity 66(10):4711–4720, which is hereby incorporated by reference, the final $OD_{600\ nm}$ was approximately 8-fold lower than with using a complex seed medium. A "complex" medium is any culture medium which contains one or more undefined components, such as a plant peptone, microbial extract or an animal source component.

Figure 1:
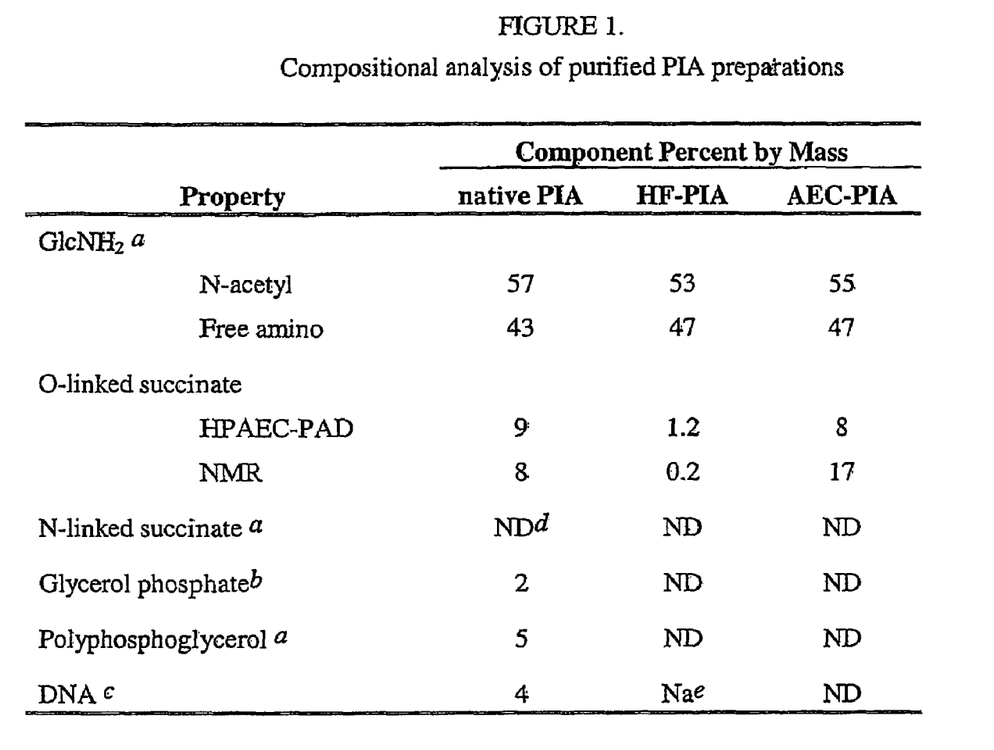

Process yields were significantly reduced using the chemically defined medium to approximately 1 mg/L. Further, use of complex medium also shortened the required fermentation time from 72 to less than 24 hours. FIG. 1 presents the results of compositional analysis for various forms of the polysaccharide.

Thus one aspect of this invention is a process for producing SAE in a Staphylococcus sp. comprising the steps of culturing the Staphylococcus on a complex medium for a time period of up to twenty-four hours, and harvesting the resultant SAE. Thus, the media should preferably contain soy peptone and/or yeast extract. Ranges for these ingredients may vary depending on the requirements of the individual organism being cultured, but in general the soy peptone may be present in amounts from approximately 5–35 g/liter, preferably about 10–30 g/liter; and more preferably about 20 g/liter. For yeast extract, ranges are from approximately 20–60 g/liter, preferably about 30–50 g/liter and more preferably about 45–50 g/liter.

Other components which should preferably be present in the medium include:

salts (such as NaCl, or KCl, 0.5–15 g/liter, preferably about 5 g/liter), buffers (such as potassium phosphate dibasic or other buffers known in the art to be useful in culture media, 1–5 g/liter, preferably about 2.5 g/liter) which provide a pH range from about 6.5 to 7.5.

an antifoam agent such as U CON LB625 (0.01–5 ml, preferably about 0.5 ml) or a silicone based antifoam agent.

other supplements such as succinic acid (at approximately 1 g/liter) and sodium succinate (approximately 1 g/liter); or other supplements commonly used in media preparation and which can be used by the bacteria as a carbon source and/or a buffer; and carbon sources, including any type of hexose and most disaccharides, preferably dextrose, should be present at about a 1% concentration.

The time of culture can vary, and is typically about 18 to 24 hours, although an extend time may be used. The culture should provide agitated cultivation conditions, the degree of aeration can be manipulated using various shaker speeds, flask configuration and culture media volumes. Such culture parameters are well known in the art.

Previous reports describing the isolation of PNSG antigen from *S. epidermidis* and *S. aureus* indicated the need for harsh extraction conditions utilizing strong acid (5N HCl) and subsequent low pH (pH 2.5) processing steps to produce a soluble product. One aspect of this invention is the discovery that these harsh extraction conditions are unnecessary and large quantities of polysaccharide can be purified from culture supernatant using a process comprising the steps of membrane ultrafiltrations (or size exclusion chromatography), enzymatic treatment for selective contaminant removal (or chromatography followed by solvent precipitation), and an optional chromatographic polishing step or anion-exchange chromatography. The polishing step removes low abundance acidic contaminants by, for example, anion exchange chromatography or by HF-treatment.

In accordance with this invention it has been also found that a high salt, low pH extraction can eliminate contamination while preserving the integrity of the isolated SAE. For this process, "high salt" means 1.5 to 3M sodium chloride or potassium chloride, preferably about 2 M sodium chloride, or if another salt is used, the concentration of that salt which would be the equivalent of 1.5 to 3M sodium chloride. Also, for this process, a "low pH" means pH 2.0–3.0, preferably about 2.5.

By way of example, the protocol of this invention resulted in overall process yields of approximately 400 mg/L culture fluid which was significantly higher than the 0.5 to 2 mg/L reported for *S. aureus* strain pCN27 by McKenny (supra).

Chemical compositional analysis by high-pH anion-exchange chromatography with pulsed amperometric detection (HPAEC-PAD) was useful for following antigen through the purification process since it could identify and quantitate glucosamine specifically, as opposed to standard colorimetric assays which were highly prone to interference from non-carbohydrate contaminants and matrix components. However, because of the required acid hydrolysis this method resulted in loss of glucosamine substituent groups and so NMR was used for structural elucidation of purified products.

Native SAE is composed of a β-1,6-linked homopolymer of glucosamine residues of which approximately 57% were substituted with acetate. No succinylation of amino groups was observed. The low amount of succinate (10%) observed by both methods was shown to be linked to sugar hydroxyl groups based on a strong downfield shift of the proton at the substituted position as well as its liability of the O-substituted esters to mild base treatment.

The SAE obtained was highly purified with the major contaminant being teichoic acid (2–5%) as identified by detection of glycerolphosphate. In addition to teichoic acid, ultraviolet (UV) absorption spectroscopy revealed the presence of a 260 nm-absorbing impurity suggestive of nucleic acids. Treatment of SAE with stripping conditions (5M NaOH, 37° C., 18 h; neutralization and diafiltration) resulted in removal of the peak at 260 nm which was consistent with the known liability of nucleic acids to base. Results from agarose electrophoresis with specific stain detection identified the contaminant as DNA. The level of presumptive DNA in the powder was 3–5% (w/w) based on 260 nm absorbance measurements. Teichoic acid impurity was detected by NMR based on polyphosphoglycerol content, and accounted for approximately 5% of the product by mass.

As previously reported by McKenney et al, 1998 *Infection and Immunity* 66:4711–4720, which is hereby incorporated by reference, BF treatment of the product was effective at removing glycerolphosphate-contaminants, but this procedure also resulted in loss of O-succinylation. Since the NMR data indicated very little change in the amount of free glucosamine amino groups before and after HF treatment, this implies that BF-SAE is a more positively charged species. Anion exchange chromatography (AEC) provided a chemically mild alternative to BF and was highly effective in reducing teichoic acid and DNA to non-detectable levels while yielding a high product recovery of 80–90%. AEC-SAE retained its original chemical composition including maintenance of O-succinylation. The higher value observed by NMR resulted from the supernatant of incomplete solubilized AEC-SAE in $D_2O$ after lyophilization. Since the succinate was completely liberated by base treatment and some polysaccharide was invisible to NMR due to its poor solubility, this resulted in the apparently higher succinate ratio.

The percentage of O-substituted succinic acid was determined on the sample in alkaline solution where O-succinate was hydrolyzed to free succinate. The well resolved peak of free succinate at approximately 2.39 ppm was integrated, and its ratio over polysaccharide repeating units, represented by the anomeric peaks (4.3–4.6 ppm) was calculated as O-succinate percentage.

Both Native-SAE and AEC-SAE make up further aspects of this invention.

Figure 2:
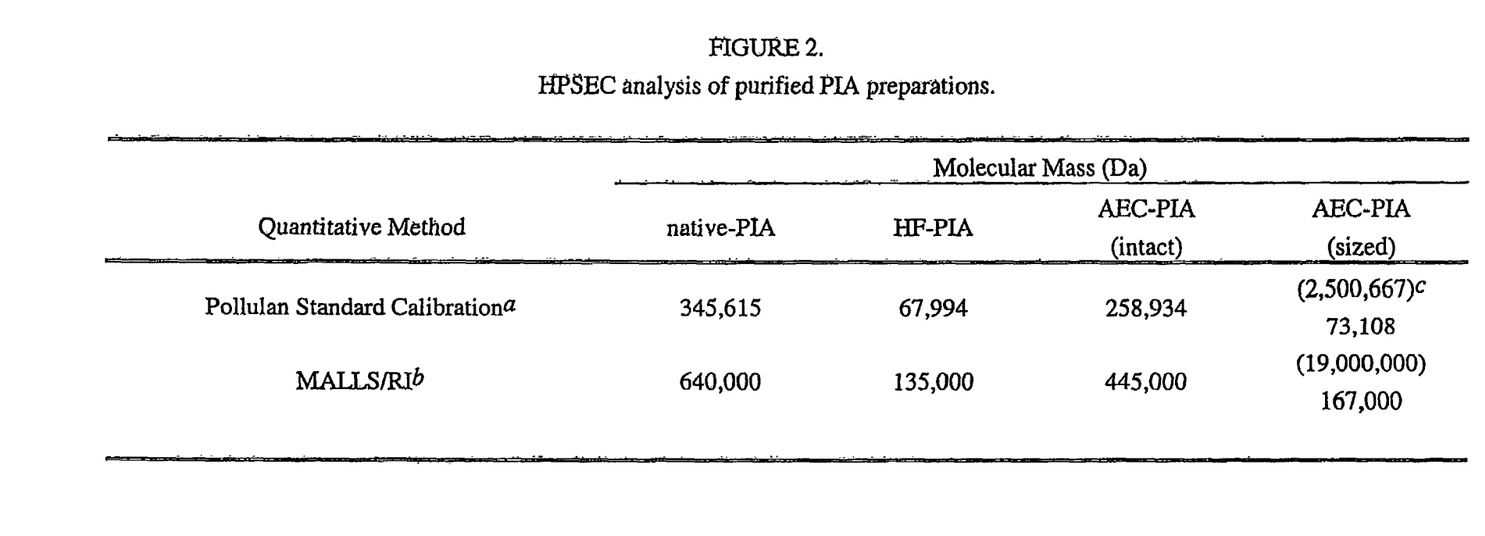

Sizing analysis of SAE. To judge the effect of different treatments on polymer size, relative comparisons were made using both calibration with pollulan standards and multi-angle laser light scattering (MALLS). FIG. 2 shows the estimated molecular masses of the various forms determined by each method. In all cases the MALLS values were roughly twice as high as those determined by elution time relative to standards. Light scattering measurements are sensitive to low abundance contaminants, and even very low concentrations of a high $M_r$ species can seriously skew results toward the high end limit of mass. To minimize these effects, sharp cuts were taken at the apex of the refractive index peak, but bleed-in from the high $M_r$ components was still possible. This explanation is supported by the observation that the mass of the small leading edge peak present in the AEC-sized SAE was nearly 10-fold higher in mass when quantitated by MALLS. Another factor contributing to the discrepancy involved the dn/dc term used to calculate $M_r$ from the scatter data. The detector was calibrated relative to a low mass pollulan using a value of 0.133 for dn/dc [Bednar, et al, 1993 *Carbohydrate Research*, 243:115–130, which is hereby incorporated by reference]. This term reflects, in part, molecular shape of the chromatographic analyte, and it is conceivable that the shapes of SAE and the pollulans were significantly different.

Native SAB was isolated as a high $M_r$ polymer of greater than 300,000 Da. AEC was used for removing non-covalently electrostatically associated acidic contaminants. Treatment of native SAE with HF resulted in considerable hydrolysis with a concomitant size reduction of 5–10 fold. Physical sizing of AEC-SAE by sonication was employed in order to control the total reduction obtained and to avoid chemical alteration of the antigen. The conditions employed resulted in a preparation with $M_r$ comparable to HF-treated material. Based on analytical HPSEC of the intermediate sonication timepoints the reduction process was fairly linear. It is unclear why the AEC-sized material contained a low abundance peak of very high $M_r$. It is conceivable that under the inputted energy conditions a small amount of radical-induced polymerization may have proceeded as a minor side reaction.

Figure 3:
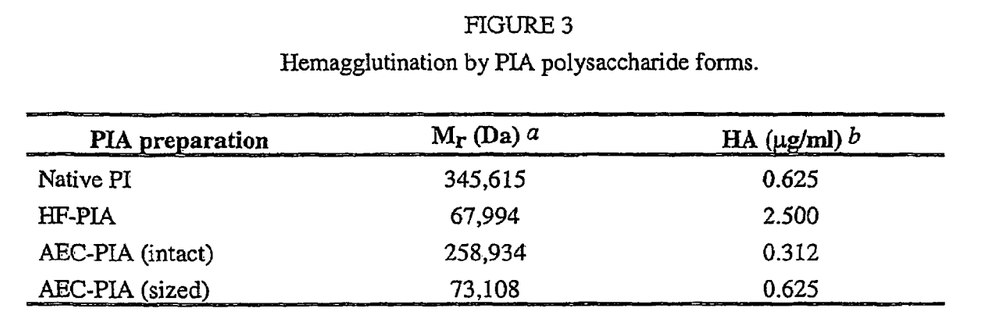

Hemagglutination assays. The PIA expressed by S. epidermidis strains has been shown by others to be responsible for their ability to agglutinate red blood cells Thus, the hemagglutination assay can be used as an in vitro functional assay for the different polysaccharide preparations. FIG. 3 summarizes the minimum concentration of each SAE form required to agglutinate red blood cells. The HF-treated SAE showed the poorest ability to hemagglutinate, requiring a four to eight-fold higher concentration for hemagglutination than any of the other preparations. HF-treated SAE was both more positively charged than the other forms and had a low molecular mass. There appears to be little difference in hemagglutination between the remaining preparations, even though they differed in size by as much as 5-fold. The size of the purified PIA described by Mack, et al was approximately 28,000 Da. Our data suggests that charge of the molecule may be more important for this function than size. The possibility remains that the smaller the molecular mass, the less able the polysaccharide is to cause agglutination.

NMR analysis of N-linked substituents. The fact that previous reports had speculated that the protective efficacy of PNSG was dependent on N-succinylation led us to closely investigate the nature of the substituted GlcNH2 residues. In order to prepare authentic standards for NMR analysis, native SAE was stripped of its N- and O-linked substituents by treatment with base. Complete succinylation of available glucosamine amino groups and some O-succinylation was obtained by reaction with succinic anhydride. The N+O succinyl SAE could be selectively stripped of O-succinate by incubation under mildly basic conditions for 2 hours. Under these conditions amino group substitution was preserved as determined by lack of ninhydrin activity.

Figure 4:
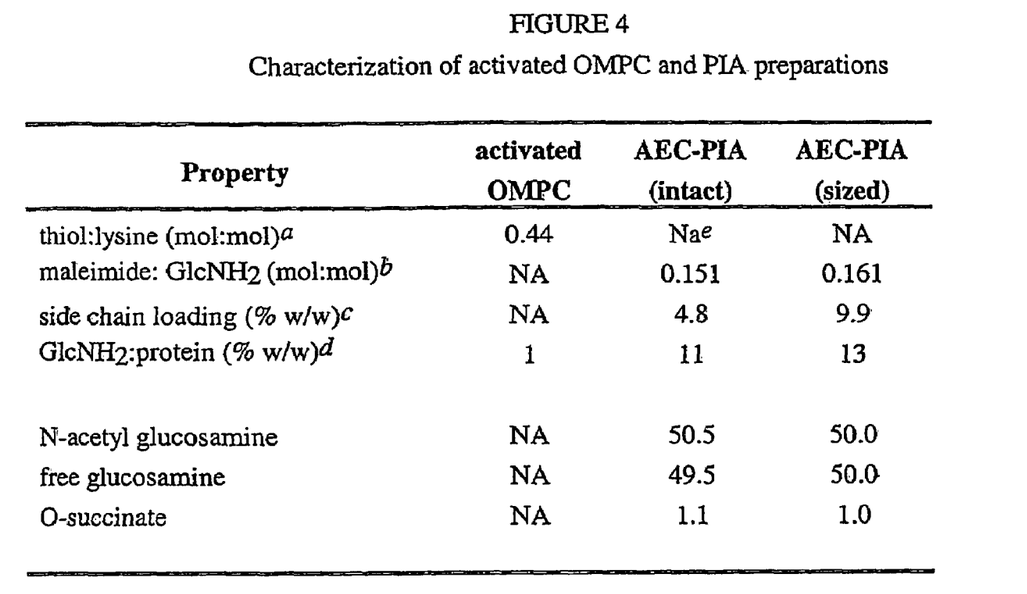
Figure 5:
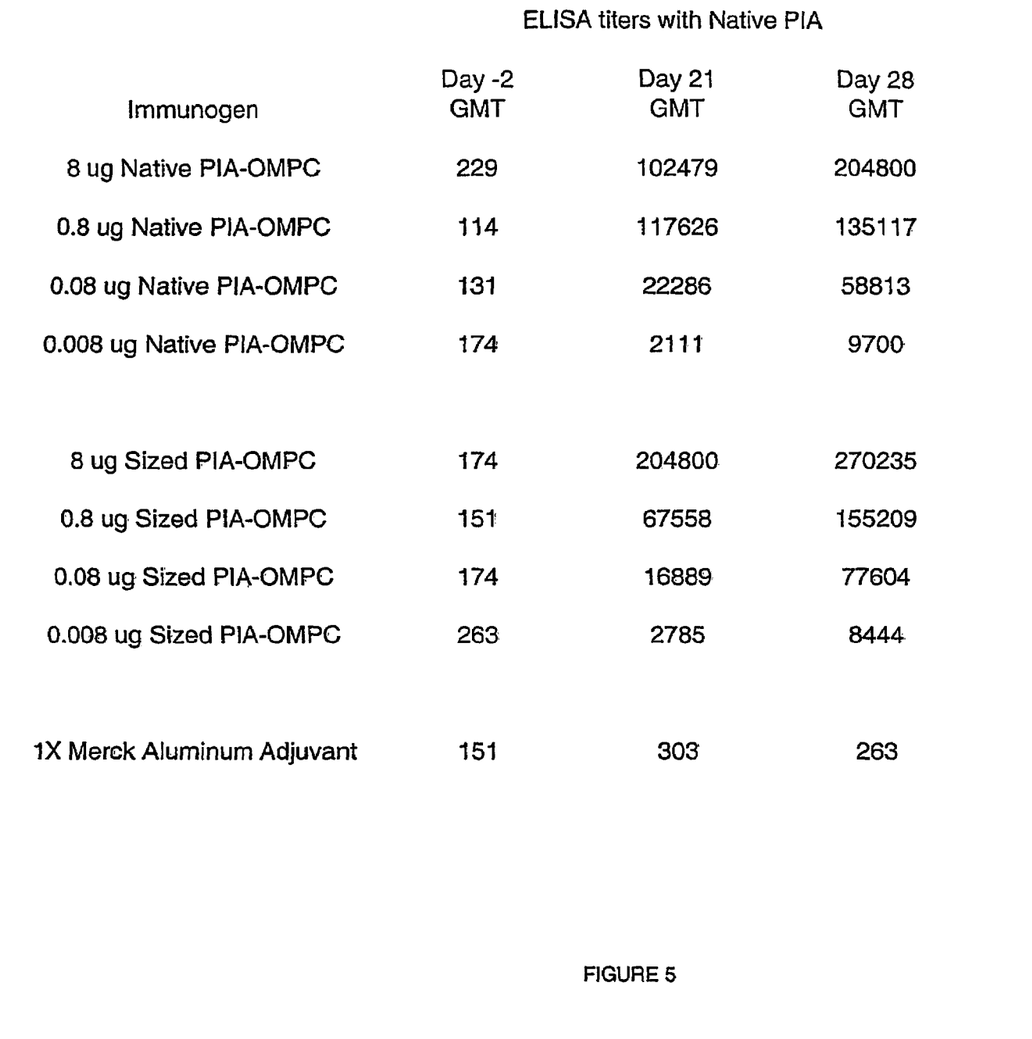
FIG. 5 gives ELISA titres of native SAE after various times in mice.

Conjugation of SAE to OMPC. The AEC-processed intact and sized forms of SAE were activated to introduce a sulfhydryl-reactive maleimide group and subsequently conjugated to thiolated OMPC protein. FIG. 4 summarizes the analytical characterization of conjugates and activated intermediates. The large, particulate nature of OMPC allowed the use of ultracentrifugation for removal of excess reagents and unconjugated polysaccharide. The thiolation conditions used produced an activated OMPC with 43% of theoretical surface-accessible lysines derivatized. The product was stable with a loss of less than 10% of sulfhydryl reactivity over 70 hr at 4° C. Polysaccharide activation resulted in side chain loadings of 4.8% and 9.9% for the intact and sized forms, respectively. Activated polysaccharide and protein were mixed at a defined maleimide to thiol ratio of 0.5 to 1, which preliminary experiments had shown yielded 10–20% SAE by weight.

Compositional analysis indicated that these targets were achieved for both intact (11%) and sized (13%) preparations. Stringent washing conditions using high salt and detergent were found to be necessary to effect removal of more than 95% of unconjugated polysaccharide. The conjugates were adsorbed to alum adjuvant at 0.5 mg/ml at which concentration they were greater than 99% adsorbed. Routine stability monitoring of the bulk alum product was performed by pelleting an aliquot and measuring the protein in the supernatant fraction. No detectable protein was observed after 45 days at 4° C. storage.

The present invention is also directed to the production of prophylactic vaccines for Staphylococcus infection. Pharmaceutically useful compositions comprising the SAEs of the present invention may be formulated according to known methods such as by the admixture of a pharmaceutically acceptable carrier. Examples of such carriers are known, such as OMPC, or alum (adsorbed onto aluminum hydroxide) Others may be found in Remington's Pharmaceutical Sciences. To form a pharmaceutically acceptable composition suitable for effective administration, such compositions will contain an effective amount of SAE.

Vaccine compositions of this invention are administered to an individual in amounts sufficient to prevent Staphylococcus infections. The effective amount may vary according to a variety of factors such as the individual's condition, weight, sex and age. Other factors include the mode of administration. Generally, the compositions will be administered in dosages ranging from about 0.5 µg to about 250 µg. The vaccines may be administered by a variety of routes, such as orally, parenterally, subcutaneously, mucosally or intramuscularly. The vaccine may be used in dosage forms such as capsules, suspensions, elixirs, or liquid solutions. The vaccine may be formulated with an immunologically acceptable carrier.

The vaccines are administered in therapeutically effective amounts, that is, in amounts sufficient to generate an immunologically protective response. The vaccine may be administered in single or multiple doses.

The following non-limiting Examples are presented to better illustrate the invention.

EXAMPLE 1

Fermentation of S. aureus Strain MN8m and Culture Inactivation

Culture broth was prepared by dissolving 300 g soy peptone, 75 g NaCl, and 37.5 g potassium phosphate dibasic in 4 L pyrogen free water (PFW). 1.5 L of dissolved Yeast Extract, ultrafiltrate grade (YEU) was added to the mixture and the volume was adjusted to 14.4 L with PFW (YEU final concentration of 31.5 gm/L). UCON LB625 antifoam (7.5 ml) was added and the medium was supplemented with 1 g/L succinic acid and 1 g/L sodium succinate. Broth was sterilized at 123° C. for 30 min after which sterile dextrose was added to a final concentration of 1%. Tryptic Soy Agar plates streaked with 0.1-mL of S. aureus MN8m (obtained from Brigham & Womens Hospital) stock were incubated overnight at 37° C. Seed medium (20 gm/L soy peptone, 5.8 gm/L NaCl, 2.9 gm/L $K_2HPO_4$, 0.46 gm/L $NaHCO_3$, and HEPES buffer (55.5 gm/L), pH 7.0, containing 1% sterile dextrose and 31.5 gm/L filter sterilized YEU) (45 ml) was inoculated with a single colony from the plates in a 300 ml Tunair flask and incubated overnight with agitation at 37° C. After overnight growth the flasks were harvested for inoculum preparation. The soy peptone/YEU media was inoculated with 40 ml MN8m inoculum. The culture was agitated and sparged with air to maintain dissolved oxygen at 30%. Temperature was maintained at 37° C., and pH was maintained at 7 by addition of sterile 30% NaOH. Growth was terminated when NaOH ceased to be required to maintain pH 7. For harvest, the pH was adjusted to 5 with 50% acetic acid and $MgCl_2$ was added to 0.1M. The culture was heated to 60° C. and held for 90 min. The inactivated culture was centrifuged at 13,600×g for 10 min and supernatant was retained for further processing.

EXAMPLE 2

Purification of SAE Antigen

Conditioned supernatant (11.2 L) was clarified by filtration using Suporcap-100 0.8/0.2 micron cartridges (Pall Gelman, Ann Arbor, Miss.) and then concentrated by tangential flow filtration (TFF) using a 500K molecular weight cutoff (MWCO) hollow-fiber membrane cartridge (AIG Technologies, Needham, Mass.) to a volume of 700 mL. Following concentration, the retentate fraction was diafiltered against. 8 volumes of distilled deionized (DI) water. The retentate was adjusted to 5 mM Tris-HCl, pH 8, 2 mM $CaCl_2$, and 2 mM $MgCl_2$. Proteinase K (14 mg) was added and the mixture was allowed to incubate for 16 hours at 20° C. The digestion reaction was adjusted to 2M NaCl and concentrated to 700 mL by TFF as previously described. The retentate was successively diafiltered against 8 volumes of 2M NaCl, 8 volumes of Low pH Buffer (25 mM sodium phosphate, pH 2.5, 0.1M NaCl), and 10 volumes of DI water, after which it was concentrated to a final volume of 340 mL. The concentrate was shell-frozen in pre-weighed bottles and lyophilized to dryness to generate native SAE antigen.

EXAMPLE 3

Polishing and Sizing of Native SAE

Native SAE (1 g) was dissolved at 2 mg/ml in 10 mM HEPPS, 0.4 M NaCl, pH 7.7 buffer by stirring overnight at ambient temperature. Residual insolubles were removed by centrifugation at 13,000×g for 30 min at 20° C. The supernatant fraction was applied to a 0.9 L column (11.3 cm id×9 cm) of Fractogel EMD TMAE(M) resin (E.M. Sciences, Gibbstown, N.J.) equilibrated in 10 mM HEPPS, 0.4 M NaCl pH 7.7 buffer at 40 ml/min. The column was washed with 3 volumes of equilibration buffer and eluted with 10 mM HEPPS, 2 M NaCl, pH 7.8 buffer. Fractions of 100 ml were collected and scanned over the wavelength range 340 to 240 nm. Flow-through fractions which showed no absorbance maximum at 260 nm were pooled and diafiltered against 18 volumes of DI water at ambient temperature using a BIOMAX 50 K MWCO membrane (Millipore, Bedford, Mass.). Size reduction was effected using a cup and horn sonication apparatus (Misonix, Farmingdale, N.Y.) employing a power output of 6.5, a 2 second cycle rate, and a duty cycle of 50%. The sample was kept cool by a constant flow of water through the apparatus. Time-dependent molecular weight reduction was monitored by HPSEC at 30, 45, 60, 75, 90, and 110 minutes at which point sonication was terminated.

EXAMPLE 4

HF Treatment of Native SAE

Native SAE (101 mg) was dissolved in DI water at 5 mg/ml. An equal volume of 48% HF was added after which the sample was mixed by inversion and incubated at 4° C. for 25 hr. The reaction was diluted with an equal volume of DI water and the pH was adjusted to neutrality by addition of 50% NaOH. The sample was dialyzed against hot DI water (65° C.) for 22 hr using 8 K MWCO tubing. It was then dialyzed a further 24 hr against 2 changes of DI water at ambient temperature. The reaction mixture was shell-frozen in pre-weighed bottles and lyophilized to dryness.

EXAMPLE 5

Preparation of N-Succinylated SAE

In order to effect removal of N and O-linked substituents native SAE was dissolved at 4 mg/ml in argon-sparged 5N NaOH and incubated under argon for 18 hr at 37° C. The reaction mixture was cooled to $\leq 10°$ C. in an ice water slurry and neutralized by slow addition of ice cold 5N HCl. The reaction was concentrated 3-fold using a BIOMAX 50 K MWCO membrane and successively diafiltered against 5 volumes of 2.5 M NaCl and 10 volumes of DI water. The product was 0.45 μm filtered and the free glucosamine content determined by manual ninhydrin assay using standard techniques.

Succinylation of stripped polysaccharide was performed in a pH-stat set to maintain the pH at 8.5 by titration with SN NaOH. Succinic anhydride (30 mg/ml in anhydrous 1,4 dioxane) was added at a 10-fold molar excess over total glucosamine at a rate which allowed the pH stat to maintain a pH of 8.2 to 8.5. The reaction was incubated for 4 hr at ambient temperature. For total N-succintlated and some O-succinylated product the reaction was made 2.5 M in NaCl and successively diafiltered against 6 volumes 2.5 M NaCl and 10 volumes DI water. For N-succinylated only product, the reaction was adjusted to pH 12 and incubated for 2 hr at ambient temperature. It was then diafiltered as for the N+O product.

EXAMPLE 6

Polysaccharide Analysis

Polysaccharide analysis was carried out on a high field NMR instrument. To simplify the spectrum due to O-substituted succinate, the sample was dissolved in $D_2O$ at pH~12. DSS-d6 was spiked in the sample as a reference of chemical shift (0 ppm). The spectrum was acquired at 20° C. The spectral width was at least 6 ppm to cover all the interested proton peaks.

The percentages of $GlcNH_2$ and GlcNAc were determined from the peak integration of anomeric protons on these residues. The O-substitution percentage was based on the ratio of the peak integration of liberated succinate and anomeric proton.

The linkages of polysaccharide was determined with long range heteronuclear correlated spectrum, HMBC (Abeygunawardana et al. 1993 *Advances in Biophysical Chemistry* 3:199–249, which is hereby incorporated by reference.) The cross peaks across the glycosidic linkage indicated 1→6 linkage.

The anomeric configuration of sugar residues was determined by measuring the $^3J_{H1H2}$ coupling constant. The large coupling constant (8–9 Hz) indicated a β anomeric configuration. Therefore, the polysaccharide chemical structure was determined as β(1→6)GlcNX, where X could be either $H_2$ or Ac (acetate).

Side chain loading was determined with proton 1D NMR spectrum. The proton peak of maleimide at 6.86 ppm was integrated. Its ratio over polysaccharide repeating units, represented by the peak integration of anomeric protons, determined the side chain loading.

EXAMPLE 7

Compositional Analyses

Chemical compositional analyses were performed by high-performance anion-exchange chromatography using an alkaline elution protocol combined with pulsed amperometric detection (HPAEC-PAD). SAE samples were hydrolyzed in 6N HCl at 95° C. for 72 h after which the hydrolysate was evaporated to dryness and reconstituted in 200 µl of DI water. Monosaccharide compositional analysis was performed on a BioLC GP50 system equipped with an ED40 Electrochemical Detector (Dionex, Sunneyvale, Calif.). Chromatography was performed at room temperature on a CarboPac PA1 column (4 mm i.d.×250 mm) at a flow rate of 1 ml/min using the elution scheme: (a) isocratic at 18 mM NaOH for 19 min; (b) wash at 100 mM NaOH for 11 min; (c) restoring of the isocratic condition at 18 mM NaOH for 15 min.

Glycerophosphate and succinate analyses were performed at room temperature on a Ionpac AS 11 column (4 mm i.d.×250 mm) at a flow rate of 1 ml/min using the elution scheme: (a) isocratic at 4 mM NaOH for 5 min; (b) gradient from 4 to 10 mM NaOH in 10 min; (c) step gradient from 10 to 20 mM NaOH in 0.1 min; (d) wash at 50 mM NaOH for 14 min; (e) restoring of the isocratic condition at 4 mM NaOH for 10 min.

EXAMPLE 8

High Performance Size Exclusion Chromatography (HPSEC)

Relative molecular weights of polysaccharide preparations were determined on a Alliance 2690 HPLC system (Waters, Milford, Mass.) using two Waters ULTRAHYDROGEL Linear columns (7.8mm i.d.×300 mm) linked in series behind a guard column and a 250 Psi flow restrictor. Chromatography was performed in 0.1 M sodium phosphate pH 7.2 buffer containing 0.05% sodium azide at a flow rate of 0.5 ml/min. Detection was by refractive index using a Waters 410 differential refractometer. Pollulan molecular weight markers (Polymer Laboratories, Amherst, Mass.) were used to calibrate the system Multi-angle laser light scattering (MALLS) data was generated using a dual angle Precision Detectors PD2000DLS system calibrated with the 47,300 Da pollulan standard.

EXAMPLE 9

Hemagglutination Assay

For assay of whole bacteria, S. epidennidis strain RP62a cells were grown overnight on TSA plates and suspensions from these plates were subcultured for 3–5 hours in TS broth in shake flasks at 37° C. Cells were harvested, washed once in PBS, and suspended in PBS to an $OD_{650\ nm}$ of 1. A 1% sheep red blood cell (SRB) suspension was made by reconstituting lyophilized SRB (Sigma, St. Louis, Mo.) in PBS, 1% BSA. Bacterial suspension (50 µl) was added to a 96 well microtiter plate, and subsequent 2-fold dilutions of bacteria were made in PBS. Then 50 µl of 1% SRB was added to each well and the plate was incubated without mixing at room temperature for 2 hours before visual examination.

For assay with SAE preparations, 50 µl of polysaccharide at a concentration of 10 µg/ml was added to a 96 well microtiter plate, and subsequent 2-fold dilutions were made in PBS. 50 µl of 1% SRB was added to each well and the plate was incubated without mixing at room temperature for 2 hours before visual examination. A positive result was defined as the dilution of bacteria or poly-saccharide that produced diffuse red blood cells with no red blood cells pelleting at the bottom of the well.

EXAMPLE 10

Preparation of SAE-OMPC Conjugates

OMPC carrier protein was activated by thiolation of available lysine residues using a standard technique with minor modifications. Briefly, OMPC (70 mg) was pelleted by centrifugation at 289,000×g for 90 min and resuspended at 10 mg/mL in 0.1M sodium borate buffer, pH 11.3 using a Dounce homogenizer. For thiolation, 40 mg of EDTA and 8 mg of DTT were dissolved in 1.4 mL pH 11 buffer and 63 mg of N-acetyl homocysteine thiolactone was dissolved in 0.7 mL $H_2O$. The solutions were added to the OMPC and the reaction mixture was incubated for 2 hrs under $N_2$ at room temperature. The thiolated OMPC was pelleted as above, washed with 20 mM HEPES, 2 mM EDTA, 150 mM NaCl, pH 7.3, (HEPES/EDTA) and repelleted. The pellet was resuspended at 10 mg/mL in HEPES/EDTA and the thiolated OMPC was centrifuged at 1,000×g for 5 min at 4° C. to pellet any aggregated material.

Polished or polished and sized SAE was activated for conjugation by introduction of a maleimide group using the heterobifunctional reagent sulfo-succinimidyl 4-(N-maleimidomethyl)cyclohexane-1-carboxylate, sSMCC (Pierce, Rockford, Ill.). Solid sSMCC was added to the polysaccharide dissolved in water at a 5-fold molar excess over SAE free glucos amine (as determined by NMR). The reaction was adjusted to pH 7.8 by addition of HEPPS to a final concentration of 35 mM. The reaction was incubated in the dark at room temperature for 3 hours. The reaction mix was concentrated and diafiltered against HBS using a 10 K Pellicon flat sheet membrane. Maleimide incorporation was determined by quantitation of thiol consumption. Activated polysaccharides were snap frozen and stored at −70° C. prior to conjugation.

For conjugation, polysaccharides were thawed and mixed with thiolated OMPC at a 0.5 to 1 molar ratio of maleimide to sulfhydryl. The pH was adjusted to 7 by addition of HBS and reactions were incubated for 15 to 20 hr at room temperature in the dark. To quench residual thiols, iodoacetamide was added at a 10 fold molar excess over total sulfhydryl, and the reactions were incubated for 15 to 20 hr at room temperature in the dark. To quench residual maleimides, N-acetyl-cysteamine was added at a 5-fold molar excess over iodoacetamide and incubated as above. To remove excess reagents and residual free polysaccharide conjugates were pelleted by centrifugation at 289,000×g for 60 min, resuspended in TED buffer (0.5% w/v deoxycholate in 0.1M Tris-HCl, 0.01M EDTA, pH 8.5 buffer) using a dounce homogenizer, and incubated for 15–20 hr at room temperature. The conjugates were pelleted and resuspended twice in 20 mM HEPES, pH 7.3 buffer containing 0.5M NaCl. After a final re-pelleting they were resuspended in HBS and centrifuged at 1000×g for 10 minutes to remove any aggregated material. Protein was determined by a modified Lowry assay and polysaccharide content by Dionex analysis.

Conjugates were adsorbed onto alum adjuvant at a final concentration of 0.5 mg/ml by mixing a 2× stock and 2× alum at room temperature for 45 minutes. The alum-ad- sorbed bulk was formulated for animal studies by preparing vaccine stocks at 80, 8, 0.8, and 0.08 µg/ml polysaccharide. Bulk alum product was diluted with 1× alum diluent to achieve the final desired concentrations.

EXAMPLE 11

Figure 6A:
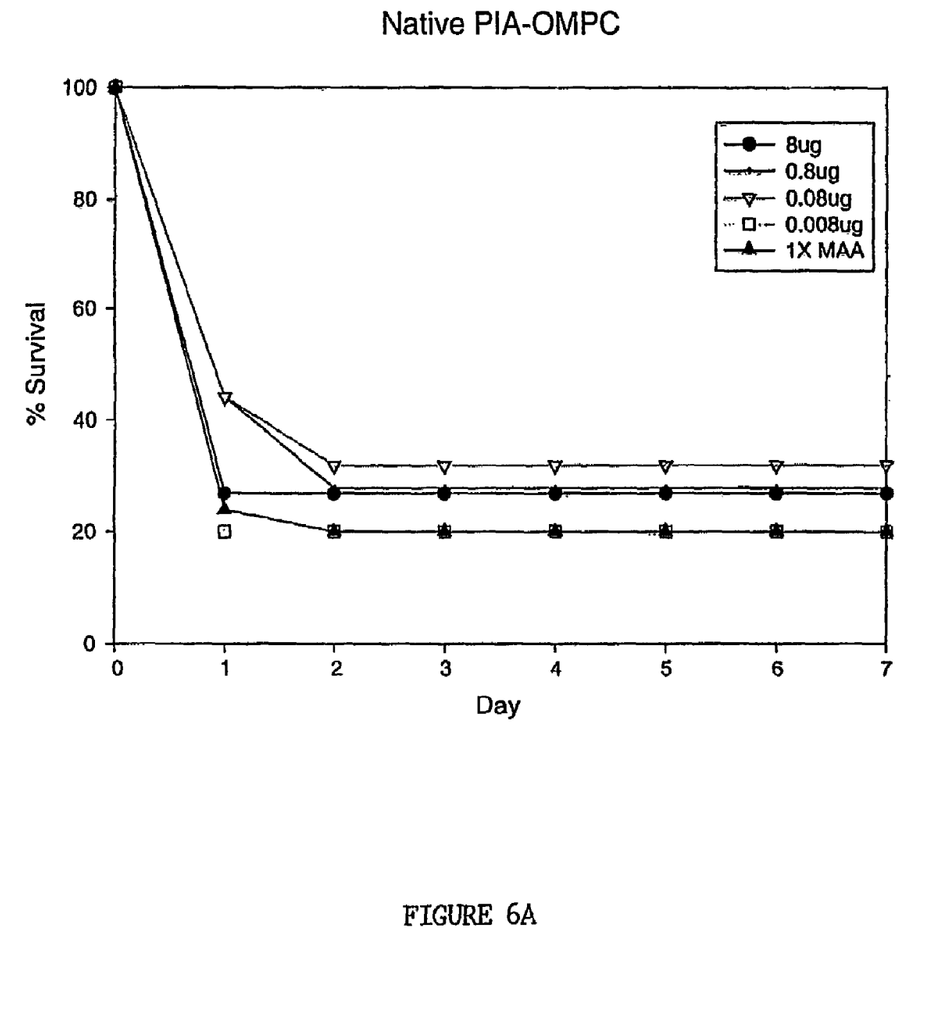
Figure 6B:
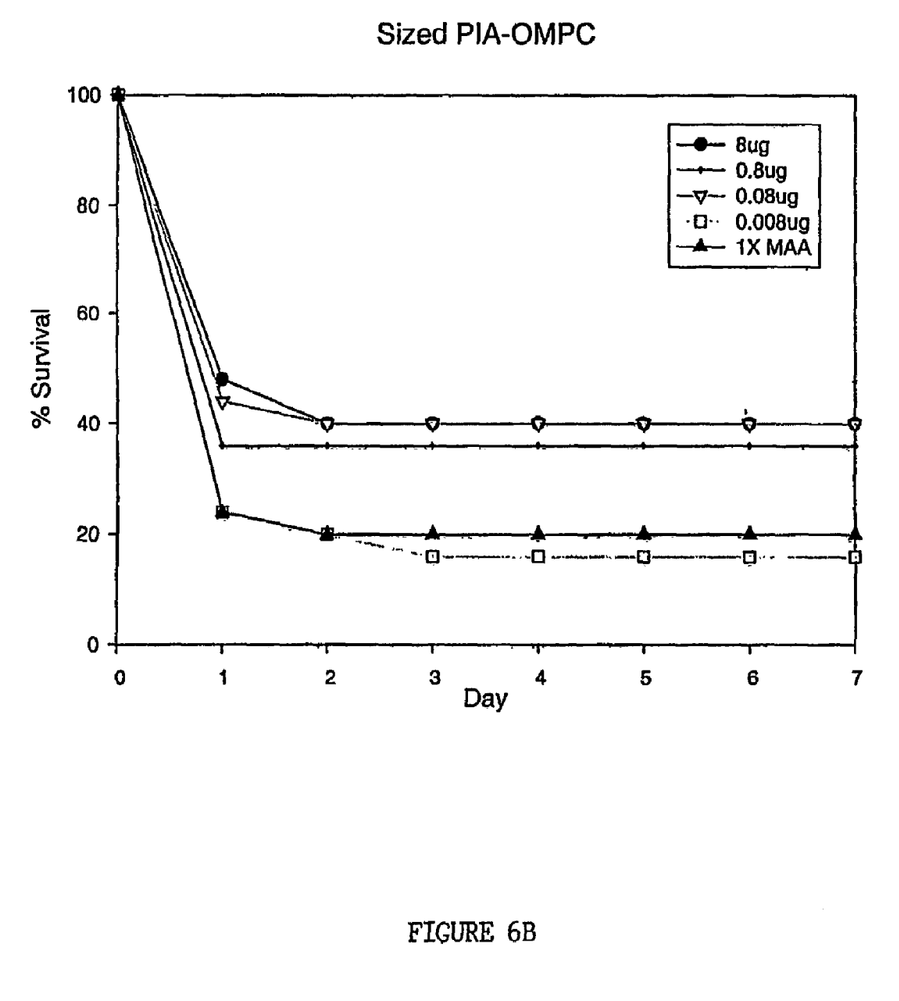

Balb/c mice (4–5 weeks old) were rested for one week and then immunized with 0.05 µl into backs of both thigh muscles with Native SAE-OMPC and Sized SAE-OMPC formulated in 1× Merck Aluminum Adjuvant. The animals were divided into 8 groups of 25 mice and each group received 8, 0.8, 0.08 or 0.008 µg/mouse of either Native or Sized versions of the SAE-OMPC conjugated antigen adsorbed onto 1× Merck Aluminum Adjuvant. A separate group of 25 mice were immunized with 1× Merck Aluminum Adjuvant alone. The groups were immunized with the antigens on Day 0 and Day 14. Blood from a subset of animals was collected at Day −2, Day 21 and day 28. The animals were challenged with 9.88×10$^8$ CFU of *S. epidermidis* strain RP62A by IP injection. The number of animals that survived the challenge was followed for 7 days, and is shown in FIGS. 6A and 6B.

What is claimed:

1. An isolated *Staphylococcus aureus* exopolysaccharide (SAE) having the formula wherein 40–60% of $R_1$ is H and the remainder of $R_1$ is COCH$_3$, and 75–95% of $R_2$ is H and the remainder of $R_2$ is an O-linked succinate and n is such that the molecular weight is at least about 300,000 Da.

2. A SAE according to claim 1 wherein 45–55% of $R_1$ is H, and 85–95% of $R_2$ is H.

3. A SAE according to claim 2 wherein 50% of $R_1$ is H, and 85–95% of $R_2$ is H.

4. An immunogenic composition comprising a SAE according to claim 1.

5. A composition according to claim 4 in a physiologically acceptable salt solution.

6. An immunogenic composition comprising a SAE according to claim 1 covalently coupled to an immunogenic protein carrier.

7. A composition according to claim 6 further comprising an immunostimulatory adjuvant.

8. A method of inducing an immune response in an animal comprising administering an immunogenic composition of claim 4.

9. A method of inducing an immune response in an animal comprising administering an immunogenic composition of claim 6.

10. A method of making a SAE compound according to claim 1, comprising the steps of:
    a) concentrating medium obtained from a *S. aureus* culture to obtain a concentrated medium;
    b) filtering the concentrated medium to obtain a retentate; and
    c) digesting the retentate with a protease to obtain the SAE compound.

11. A method according to claim 10, further comprising the steps of:
    d) concentrating the SAE using diafiltration.

12. A method of making a SAE compound according to claim 10, wherein step a) comprises concentrating medium obtained from a *S. aureus* culture using tangential flow filtration.

13. A method of making a SAE compound according to claim 10, wherein step b) comprises a diafiltration step.

* * * * *